(12) United States Patent
Burrow et al.

(10) Patent No.: US 8,127,575 B2
(45) Date of Patent: Mar. 6, 2012

(54) WICKING FABRIC AND GARMENT MADE THEREFROM

(75) Inventors: Thomas Richard Burrow, Derby (GB); Heinrich Firgo, Vöcklabruck (AT)

(73) Assignee: Lenzing Aktiengesellschaft, Lenzing (AT)

( * ) Notice: Subject to any disclaimer, the term of this patent is extended or adjusted under 35 U.S.C. 154(b) by 330 days.

(21) Appl. No.: 12/067,470

(22) PCT Filed: Sep. 22, 2006

(86) PCT No.: PCT/GB2006/003534
§ 371 (c)(1),
(2), (4) Date: May 29, 2008

(87) PCT Pub. No.: WO2007/034204
PCT Pub. Date: Mar. 29, 2007

(65) Prior Publication Data
US 2009/0133446 A1    May 28, 2009

(30) Foreign Application Priority Data
Sep. 23, 2005   (GB) .................................... 0519462.6

(51) Int. Cl.
*A41B 9/06* (2006.01)
(52) U.S. Cl. .......................................... 66/176; 66/202
(58) Field of Classification Search ............ 66/202, 66/169 R, 170, 178 R, 196
See application file for complete search history.

(56) References Cited

U.S. PATENT DOCUMENTS

| | | | |
|---|---|---|---|
| 4,465,730 A * | 8/1984 | Okada ........................... 442/243 |
| 4,837,078 A | 6/1989 | Harrington | |
| 5,065,600 A * | 11/1991 | Byles ................................ 66/193 |
| 5,209,084 A | 5/1993 | Robinson et al. | |
| 5,269,720 A | 12/1993 | Moretz et al. | |
| 5,273,596 A | 12/1993 | Newkirk | |
| 5,297,296 A | 3/1994 | Moretz et al. | |
| 5,312,667 A * | 5/1994 | Lumb et al. ...................... 428/91 |
| 5,319,807 A | 6/1994 | Brier | |
| 5,433,987 A | 7/1995 | Peterson et al. | |
| 5,547,733 A * | 8/1996 | Rock et al. ........................ 428/91 |
| 5,735,145 A * | 4/1998 | Pernick ............................ 66/196 |
| 5,787,503 A * | 8/1998 | Murphy, III ..................... 66/171 |
| 6,427,493 B1 * | 8/2002 | Kasdan et al. ............... 66/169 R |

(Continued)

FOREIGN PATENT DOCUMENTS

DE   4336303 A1 *   4/1995

(Continued)

OTHER PUBLICATIONS

Wang Xiaobing et al., "Design of Fabric for Functional Sports Wear", Northwest Institute of Textile, vol. 37, pp. 477, 478 and 451, Oct. 1991.

(Continued)

*Primary Examiner* — Danny Worrell
(74) *Attorney, Agent, or Firm* — Howson & Howson LLP

(57) ABSTRACT

A moisture wicking fabric has one side comprised substantially entirely of inherently hydrophobic fibers such as polyester or polypropylene and the other side comprised of a mixture of hydrophobic fibers such as polyester or polypropylene and hydrophilic fibers, particularly cellulosic fibers such as cotton, lyocell and viscose rayon. A garment can be formed from such a moisture wicking fabric, for example by the whole garment knitting method, the side comprised of the mixture of fibers being the external side of the garment.

19 Claims, 1 Drawing Sheet

U.S. PATENT DOCUMENTS

| | | | |
|---|---|---|---|
| 7,360,378 B2 * | 4/2008 | Foshee | 66/196 |
| 7,552,603 B2 * | 6/2009 | Dahlgren | 66/185 |
| 2003/0181118 A1 | 9/2003 | Ko et al. | |
| 2004/0058072 A1 | 3/2004 | Rearick et al. | |
| 2005/0282455 A1 * | 12/2005 | Foshee | 442/318 |

FOREIGN PATENT DOCUMENTS

| | | |
|---|---|---|
| JP | 06-184885 A | 7/1994 |
| JP | 09-031823 A | 2/1997 |
| JP | 10-025642 A | 1/1998 |
| JP | 2002-054056 A | 2/2002 |
| JP | 2003-013344 A | 1/2003 |
| WO | 98/24621 A1 | 6/1998 |
| WO | 2004/089614 A2 | 10/2004 |

OTHER PUBLICATIONS

English translation of Office Action dated May 31, 2011 issued by the Japanese Patent Office in corresponding Japanese Patent Application No. 2008-531787.

* cited by examiner

WICKING FABRIC AND GARMENT MADE THEREFROM

FIELD OF THE INVENTION

This invention relates to wicking fabrics and has particular reference to wicking fabrics containing lyocell and/or other cellulosic fibres. It also relates to garments formed of such wicking fabrics.

There is a considerable demand for technical or active fabrics, particularly for use in sportswear or other applications, where moisture is required to be transported rapidly and comfortably from one side of the fabric to the other and then to be spread over a wide surface area to maximise the cooling effect due to evaporation. Such fabrics are then also faster drying than normal fabrics.

These technical fabrics not only need to be effective in terms of their wicking abilities but they also preferably need to be comfortable in use. Ideally, such fabrics, when made up into garments, feel drier on the inside of the garment than on the outside. They are also preferably not too heavy to the extent that they feel uncomfortable in use.

BACKGROUND ART

In one form of known prior art the fabrics are made of polyester produced in two layers, with an inner layer being completely formed of a hydrophobic form of polyester and the outer layer being formed of treated polyester which is hydrophilic. These hydrophilic treatments are applied as chemical treatments to the polyester, and unfortunately it has been found that the fabrics lose their hydrophilic treatment on washing and they therefore deteriorate from both a comfort viewpoint and a technical performance viewpoint.

Hydrophobic materials may be weakly hygroscopic, such as polyesters and polyacrylonitriles, which have a low water-retention of less than about 25%, or non-hygroscopic, such as polpropylene, polyvinyl chloride or polyethylene.

Hydrophilic materials tend also to be strongly hygroscopic, such as cellulose or wool.

It has also been proposed in published US Patent Application 2004/0058072 to produce fabrics from yarns in which there is a first yarn of cellulosic fibres, part at least of which is treated with a hydrophobic treatment, and a second yarn of cellulosic fibres with a higher absorbent capacity than the first yarn, the fabric being produced by knitting or weaving together the first and second yarns so that the inside surface has a lower absorbent capacity than the outside surface.

Again, these types of processes involve the chemical treatment of the fibres to give the desired effect, and such chemical treatments are not permanent and wash off in use.

WO-A-98/24621 discloses a unitary stratified composite, apparently for diapers or other hygienic products in which liquid from the wearer's body is to be absorbed. The composite is composed of a first stratum serving as a liquid acquisition stratum that rapidly acquires liquid from the wearer and transfers it through a transition zone to a second stratum which serves as a temporary storage medium. Both strata comprise fibres and a binding agent, and the composite in use has an outermost external surface which does not leak or absorb moisture from outside.

U.S. Pat. No. 5,433,987 discloses a spun-laced fabric having improved water absorbency to absorb perspiration and other body fluids and collect or disperse the same away from the body for the comfort or hygiene of the wearer. The fabric is used as an absorbent layer in a multilayer or laminate structure but does not form the outermost layer facing away from the wearer in use in a garment.

Other known prior art documents of lesser relevance are US-A-2003/0181118, U.S. Pat. No. 5,787,503, U.S. Pat. No. 5,735,145 and U.S. Pat. No. 5,297,296.

DISCLOSURE OF THE INVENTION

It has now been discovered that it is possible to produce technical wicking fabrics from fibres which do not require chemical treatment to be effective.

The present invention provides a moisture wicking fabric for a garment, the fabric having one outermost side comprised substantially entirely of fibres of an inherently hydrophobic material and the other outermost side comprised of a mixture of fibres of an inherently hydrophobic material and hydrophilic fibres, especially cellulosic fibres.

The invention also provides a moisture wicking fabric for a garment, the fabric having one outermost side comprised substantially entirely of fibres of an inherently hydrophobic material and the other outermost side comprised of a mixture of fibres of an inherently hydrophobic material such as a synthetic or plastics material and hydrophilic fibres such as cellulosic fibres, whereby the fabric of the one side is more hydrophobic than the fabric of the other side.

An inherently hydrophobic material is one, such as a polyester, a polyamide or a polypropylene, which has a water imbibition or retention of less than 25%.

Preferably, the inherently hydrophobic plastics material is a polyester. The fibres of the inherently hydrophobic material, e.g. plastics material, on the one side may be formed of the same material as the fibres of the inherently hydrophobic material, e.g. plastics material, on the other side or of a different material.

Preferably, the mixture of hydrophilic, especially cellulosic, fibres and fibres of an inherently hydrophobic material, e.g. plastics material, contains less than or not more than 50% of the hydrophilic, especially cellulosic, material. Preferably, the cellulosic material is lyocell, but it is also possible to use other cellulosic materials or mixtures of lyocell fibres with cellulosic materials of one or more other types, for example in lesser amounts. Typically and preferably the content of lyocell and/or other cellulosic material is in the range 10 to 50%, preferably 20 to 40% and further preferably about 30%. Staple fibres and/or continuous filaments can be used in the layers.

The fabrics may be produced by knitting or weaving or by non-woven bonding techniques such as needle-bonding. They do not require and in general do not use a binder (binding agent), which has the advantage that they are not thereby stiffened or become non-flexible. A preferred method of manufacturing the fabrics is by a knitting process, with a double-jersey knitting process being used to produce the two layers simultaneously, the layers being interlinked by a linking thread so as to be in intimate contact.

A further method of producing the fabrics is by needle-bonding, in which a layer of air-laid polyester or other hydrophobic fibres is laid over a layer of air-laid lyocell and/or other cellulosic fibres and the two layers are needle-punched together, with the needles entering from the polyester side and needle barbs being directed so as to force the polyester fibres into the lower layer of the lyocell and/or other cellulosic fibres, so as to produce on one side substantially wholly polyester and on the other side a mixture of polyester and lyocell and/or other cellulosic material.

The invention further provides a garment formed from the fabric set out above in which the side of the garment facing the wearer when the garment is worn (the inner side) comprises the substantially entirely (100%) hydrophobic layer and the other (outer) side comprises the mixture of fibres, e.g. hydrophobic fibres and cellulosic fibres. By having the side facing away from the wearer formed of the mixture of fibres, moisture contacting the garment is rapidly spread widely across the surface of the garment, whilst the hydrophobic surface contacts the wearer's skin and does not disperse perspiration so that the garment does not feel clammy to the wearer. The garment does not have backing layers on either of the two sides of the moisture wicking fabric. It may be produced by a whole garment knitting process, whereby the garment is knitted to shape as a double-jersey product in a single operation.

BRIEF DESCRIPTION OF THE DRAWINGS

Embodiments of the present invention will now be described with reference to the accompanying drawings, of which

Technical fabrics, particularly wicking fabrics suitable for uses such as sportswear, have to perform a number of processes and also have to have a good balance between aesthetics and performance. For example, sportswear formed of 100% polyester fabric is able rapidly to wick moisture from the inside of the fabric adjacent the wearer's skin to the outside. However, 100% polyester fabrics feel uncomfortable and retain virtually no water in the fabric. In particular, the fabrics only transport water from the inside to the outside and the transported moisture does not spread sideways. Thus, in regions of high production of moisture, such as in the central regions of the spine and under the arms, there is a rapid build up of water in and on the fabric, which gives an uncomfortable feel to the fabric and means that the fabric dries only slowly.

Proposals have been made to form polyester sportswear from two layers, an inner layer of 100% hydrophobic, i.e. untreated, polyester and an outer layer of fabric formed from treated polyester which has been treated to make it hydrophilic. However, such treatments are normally applied as finishes and these finishes wash off with repeated washings. Furthermore, these fabrics still have the feel or "hand" of synthetic fibre fabrics and have the normal properties of 100% polyester fabrics, namely they are prone to pilling and the build-up of static electricity.

100% cellulosic fabrics on the other hand have a different sort of problem. The water or moisture absorbency of these cellulosics is so high that the water does not spread and the fabric tends to feel wet, heavy and clammy.

Cellulosic fibres also tend to be more expensive than polyester fibres, and, therefore, the cost of the fabrics and hence of the garment tends to be greater.

Figure 1:
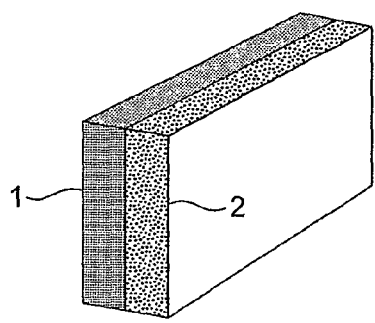
FIG. 1 is a schematic sectional view of a fabric in accordance with the present invention.

The present invention, as illustrated in FIG. 1 of the drawings, provides a moisture wicking fabric which is particularly suited to technical applications such as sportswear. The fabric comprises a two-layer structure, preferably one side of which 1 is formed almost entirely of fibres of an inherently hydrophobic plastics material such as polyester and the other side of which 2 is formed of a mixture of lyocell fibres and fibres of an inherently hydrophobic plastics material. Other cellulosic fibres such as cotton, modal or viscose rayon fibres could be used instead of or in addition to lyocell fibres, but lyocell is preferred for its combination of feel and strength, particularly wet strength.

Such a fabric produces garments which are comfortable to wear and have a high moisture wicking characteristic.

It has been particularly found that, if the layer 2 comprises a mixture of inherently hydrophobic plastics material fibres formed of polyester together with 10 to 50% by weight of lyocell, a fabric is produced which has permanent wicking properties which are not reduced by repeated washing.

To enable an understanding of the invention to take place, set out below is background information on the absorbency of fabrics, which information demonstrates the particular benefit to be obtained by using a fabric containing 10 to 50% by weight of lyocell in a polyester mix for the layer 2 referred to above.

Figure 2:
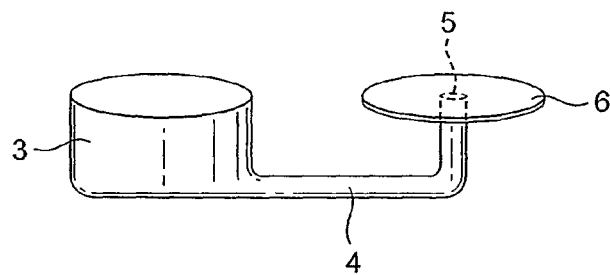
FIG. 2 is a schematic representation of a modified gravimetric absorbency testing system (GATS)

One known method of testing the absorbency of fabrics is the so-called Gravimetric Absorbency Testing System (GATS). Details of such a system are given in the journal "International Nonwoven Journal", Volume 11, No. 4, Winter 2002, in the article by Konopka and Pourdeyhimi and Kim entitled "In-Plane Liquid Distribution of Nonwoven Fabrics: Part I—Experimental Observations", particularly pages 23 to 25. Essentially, the Gravimetric Absorbency Text utilises apparatus shown schematically in FIG. 2 of the drawings, comprising a reservoir 3 for water, connected by a U-tube 4 to an outlet point 5. A disc 6 of fabric to be tested is applied over the outlet 5 so that the material of the disc 6 takes up water from the reservoir via the U-tube 4 by capillary action. However, only fabrics which absorb water will "suck" liquid into them.

Figure 3:
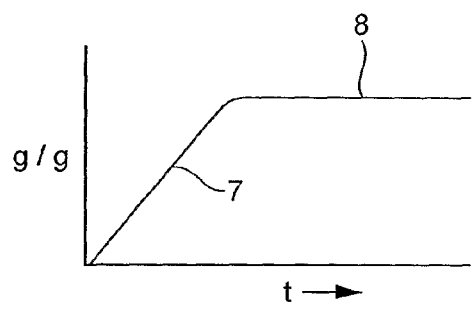
FIG. 3 is a graph of absorbency against time.

Shown in FIG. 3 of the drawing is a graph of absorbency on the vertical axis in terms of grams of water absorbed per gram of fabric against time in seconds on the horizontal axis. Essentially, the fabric absorbs water during an absorbency phase illustrated by the first portion 7 of the line of the graph until it reaches a steady state illustrated by the second portion 8 of the line of the graph. The steeper the slope 7 the greater the absorption rate of the fabric and therefore the better and quicker the fabric will absorb water. The value of the height of the steady-state line 8 is an indication of the total capacity of the fabric to absorb water. A series of tests was carried out to determine the wicking rate of the fabrics in terms of grams of water absorbed per gram of fabric per second (g/gs). The tests were carried out using various polyester/lyocell fabrics, varying from 100% polyester fabrics of untreated polyester fibre to 100% lyocell fabrics utilising increasing amounts of lyocell. The results of these tests are set out in Table 1.

TABLE 1

| % lyocell in lyocell/polyester mix | Wicking Rate (g/gs) |
|---|---|
| 0 | 0 |
| 10 | 0.06 |
| 20 | 0.16 |
| 30 | 0.267 |
| 40 | 0.4 |
| 50 | 0.444 |
| 100 | 0.444 |

Figure 4:
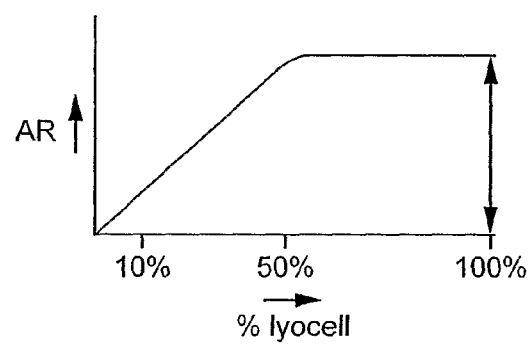
FIG. 4 is a graph of absorbency rate against percentage lyocell in a mixed lyocell/polyester material.

From these tests the absorbency rate for the different fabrics was plotted against the proportion of lyocell. This gave rise to the graph illustrated in FIG. 4 of the drawings, where the absorbency rate (AR) is measured on the vertical axis and the percentage of lyocell in the polyester/lyocell fabric mixture is measured on the horizontal axis.

It can be seen from this that the absorbency rate initially increases as more lyocell is incorporated into the fabric to reach a maximum at about 5000. Beyond 50% the absorbency rate does not increase any further.

Without prejudice to the invention, the reason for this behaviour is now believed to be because, when only a small proportion of the fibres are cellulosic (e.g. lyocell), there is unlikely to be a continuous path consisting of cellulosic fibres for the water to follow. However, when there is sufficient cellulosic fibre present the water can travel through the fabric following a continuous path of cellulosic fibres. Once each cellulosic fibre is in contact with many neighbouring cellulosic fibres, a further increase in the proportion of the cellulosic fibres will not give any increase in wicking.

This unexpected discovery has led to the present invention in which the layer 2 of the fabric comprises a mixture of lyocell (and/or other cellulosic) and polyester (and/or other synthetic). It has specifically been found that, by having the layer 2 as a mixture of polyester and lyocell, rather than 100% lyocell, water being wicked through from the polyester layer is encouraged to spread sideways through the layer 2 rather than accumulate in one place as would be the case if the layer 2 were 100% lyocell.

The lyocell in the layer 2, by wicking water away from layer 1, enhances the transpiration of the layer 1 and helps prevent garments made from the fabric feeling uncomfortable in use. It has been found by observation that water can move sideways in preferred layer 2 according to the invention at a rate of about 7.5 cm in ten seconds. This means that in less than a minute the water can move almost half a meter, in other words virtually across the entire body of a person wearing a shirt made from such a fabric. This means that, in garments formed from fabrics according to the invention, water generated in areas of high perspiration such as around the spine and under the arms can be wicked sideways in the layer 2 to enhance the comfort of the sportswear made from such a fabric. Furthermore, the surface area containing large quantities of moisture is increased by this lateral wicking, thereby enhancing the evaporation rate of the garment as a whole. Because polyester fibres are lower in weight than lyocell the fabric as a whole can be kept as a low-weight fabric, again further enhancing the comfort of the wearer.

It will be appreciated that there are many ways of making the two-layer structure, in particular the layers 1 and 2 can be woven together or they can be knitted by a double-jersey knitting process such as is described in U.S. Pat. No. 5,209,084, utilising knitting machines such as are described in the book "Dubied Knitting Manual", published by Edouard Dubied and Cie SA, Switzerland, in 1967.

By this means the layers 1 and 2 can be created simultaneously and interconnected simultaneously from yarns of polyester alone for layer 1 and a polyester/lyocell mixed yarn for layer 2. Woven and knitted fabrics are flexible and easy to wear when made up into garments such as shirts and blouses.

Figure 5:
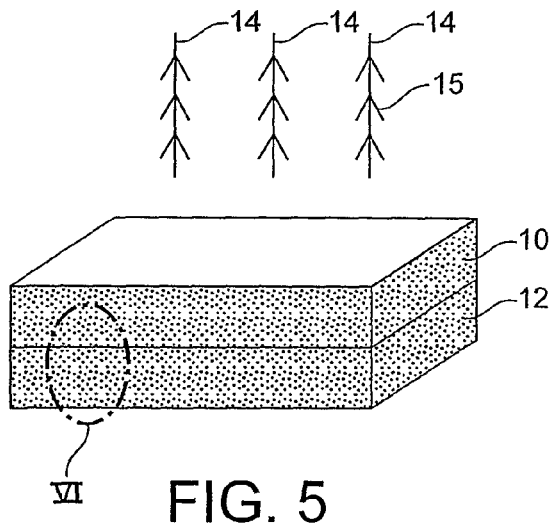
FIG. 5 is a schematic view of a needling system.
Figure 6:
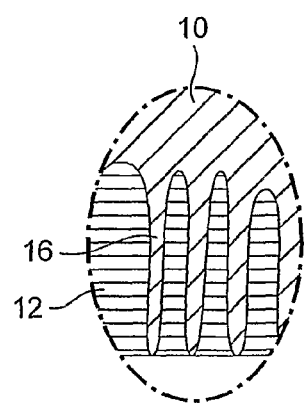
FIG. 6 is an enlargement of the portion within the oval VI of FIG. 5.

Another way of manufacturing the fabric is to needle-bond together two nonwoven webs without using a chemical binder or binding agent. As illustrated in FIGS. 5 and 6 of the drawings, a first web 10 of air-laid polyester staple fibre or air-laid polyester continuous filament is laid on top of a second layer 12. The layer 12 is an air-laid bat or mat of fibres formed from a mixture of lyocell and polyester. The two layers are then needled together by needles such as 12 which have downwardly directed barbs such as barb 15. This pushes the fibre from the upper layer 10 into the lower layer 12, as is shown more clearly in FIG. 6. Because the barbs 15 are downwardly directed, the needles tend only to push the layer 10 downwards and to a much lesser extent pull the layer 12 upwards. There is, therefore, formed a bonded structure comprising an upper layer 10 of polyester and a lower layer 12 which comprises a mixture of lyocell and polyester fibres in conjunction with additional polyester fibres pushed from layer 10. Fingers 16 shown in FIG. 6 pushing the layer 10 into the layer 12 can carry some of the polyester right through the layer 12 onto the bottom of layer 12.

In a modification of this process the layer 12 can consist entirely of lyocell fibres in the un-needle-bonded condition. This results in a mixture of lyocell and polyester, as shown in FIG. 6, which is slightly less intimately bonded than the mixture produced by starting with yarns of polyester and lyocell fibres in the layer 12. By not using a binder the fabric can be kept as flexible as possible.

Clearly, where the layer 12 is initially a blend of polyester and lyocell, the initial lyocell content in layer 12 will be greater than the lyocell content in the layer after needle-bonding, and an appropriate allowance should be made, depending on the ultimate lyocell content desired for the layer 12. These needle-bonded fabrics are not as flexible as woven or knitted fabrics even though they have no binder.

A further advantage of the present invention is that the knitting process used to form the two layers can be used to knit a complete garment in a single operation by the known whole-garment knitting process, so that the garment is made in one go from a polyester or other hydrophobic inner layer and an outer layer comprising a blend of polyester and cellulosic, typically lyocell, fibre.

Although the specific examples of the invention have been described with reference to lyocell and polyester, other hygroscopic fibres and fabrics such as other cellulosic fibres including viscose, modal and cotton, or even wool, could be used.

The hydrophobic materials include those which are non-hygroscopic or weakly hygroscopic.

The invention claimed is:

1. A moisture wicking fabric for a garment comprising two layers, the fabric having one layer consisting essentially of inherently hydrophobic fibres and the other layer comprised of a mixture of hydrophobic fibres and hydrophilic fibres, wherein said other layer forms an external side of the garment, wherein one side of the fabric is formed by a process selected from knitting and weaving and the other side of the fabric is formed by a process selected from knitting and weaving, wherein said hydrophobic fibres of said one layer and said other layer being weakly hygroscopic having water retention of less than 25% or non-hygroscopic, and wherein said hydrophilic fibres of said other layer form 10 to 50% by weight of said mixture.

2. A moisture wicking fabric as claimed in claim 1 in which the one layer of fabric is more hydrophobic than the other layer of fabric.

3. A moisture wicking fabric as claimed in claim 1 in which both sides are formed by the same process.

4. A moisture wicking fabric as claimed in claim 1 in which the one layer is formed by a different process to the other layer.

5. A moisture wicking fabric as claimed in claim 1 in which both of the layers are joined together at the same time as they are created.

6. A moisture wicking fabric as claimed in claim 1 in which each of the layers is formed separately and then conjoined to form the fabric.

7. A moisture wicking fabric as claimed in claim 1 having one layer consisting essentially of fibres of an inherently hydrophobic synthetic or plastics material and the other layer comprised of a mixture of fibres of an inherently hydrophobic synthetic or plastics material and hydrophilic fibres.

8. A moisture wicking fabric as claimed in claim 1 in which the hydrophilic fibres are cellulosic fibres.

9. A moisture wicking fabric as claimed in claim 8 in which the cellulosic fibres are selected from cotton, lyocell and viscose rayon.

10. A moisture wicking fabric as claimed in claim 1 in which the inherently hydrophobic material is selected from polyester and polypropylene.

11. A moisture wicking fabric as claimed in claim 1 in which the fibres of the inherently hydrophobic material of the one layer are formed of a different material from the fibres of the inherently hydrophobic material of the other layer.

12. A moisture wicking fabric as claimed in claim 1 in which the fibres of the inherently hydrophobic material of the one layer are formed of the same material as the fibres of the inherently hydrophobic material of the other layer.

13. A moisture wicking fabric as claimed in claim 8, in which the layer formed of the mixture of fibres contains not more than 50% cellulosic fibres and not less than 50% of fibres of an inherently hydrophobic plastics material.

14. A moisture wicking fabric as claimed in claim 13 in which the layer formed of the mixture of fibres contains 10 to 50% of cellulosic fibres.

15. A moisture wicking fabric as claimed in claim 13 in which the cellulosic fibres are lyocell fibres.

16. A garment formed of a moisture wicking fabric as claimed in claim 1 which is a knitted garment and which has been knitted by the whole garment knitting method.

17. A garment as claimed in claim 16 which is in the form of a shirt or blouse.

18. A moisture wicking fabric for a garment, consisting of:
a first layer consisting essentially of inherently hydrophobic polyester fibres being weakly hygroscopic having water retention of less than 25%, and
a second layer including a mixture of hydrophobic polyester fibres and hydrophilic lyocell fibres, said hydrophilic lyocell fibres forming 20 to 40% by weight of said mixture and being strongly hygroscopic;
said first and second layers being in intimate contact; and
one side of the fabric being formed by a process selected from knitting and weaving and an opposite side of the fabric being formed by a process selected from knitting and weaving.

19. A garment, consisting of:
a comfortable sportswear shirt made of a flexible technical fabric consisting of a two layer structure;
an inner layer of said two layer structure consisting of fibres of an inherently hydrophobic synthetic or plastics material being weakly hygroscopic having water retention of less than 25%, said inner layer forming an inner side of the garment which, when worn, contacts a wearer's skin;
an outer layer of said two layer structure being a mixture of fibres of an inherently hydrophobic synthetic or plastics material and hydrophilic fibres, said hydrophobic fibers being weakly hygroscopic having water retention of less than 25% or being non-hygroscopic and said hydrophilic fibres being strongly hygroscopic, forming 20 to 40% by weight of said mixture and being lyocell, said mixture promoting moisture to spread sideways through said outer layer across an outer surface of the outside of the garment thereby maximizing a cooling effect due to evaporation; and
said inner and outer layers being in intimate contact.

* * * * *